United States Patent [19]

Blum et al.

[11] Patent Number: 4,518,523

[45] Date of Patent: May 21, 1985

[54] METHOD FOR ADDING MAKE-UP FLUID BED OXIDATION CATALYSTS FOR FLUID BED OXIDATION CATALYSTS CONTAINING THE MIXED OXIDES OF VANADIUM AND PHOSPHORUS

[75] Inventors: Patricia R. Blum, Macedonia; Ernest C. Milberger, Solon; Mark L. Nicholas, Cleveland, all of Ohio

[73] Assignee: The Standard Oil Company, Cleveland, Ohio

[21] Appl. No.: 472,400

[22] Filed: Mar. 4, 1983

[51] Int. Cl.$^3$ .............................................. B01J 27/14
[52] U.S. Cl. .................................... 502/209; 502/210; 502/211; 502/213; 549/259; 549/260
[58] Field of Search ................ 252/435, 437; 502/209, 502/210, 211, 213

[56] References Cited

U.S. PATENT DOCUMENTS

| | | | |
|---|---|---|---|
| 3,888,886 | 6/1975 | Young et al. | 252/435 X |
| 3,915,892 | 10/1975 | Harrison | 252/435 |
| 3,975,300 | 8/1976 | Burress | 252/437 X |
| 3,985,775 | 10/1976 | Harrison | 252/437 X |
| 4,092,269 | 5/1978 | Mount et al. | 252/435 |
| 4,116,868 | 9/1978 | Mount et al. | 252/435 X |
| 4,132,670 | 1/1979 | Katsumoto et al. | 549/259 X |
| 4,147,661 | 4/1979 | Higgins et al. | 252/435 |
| 4,165,299 | 8/1979 | Pedersen | 252/435 |
| 4,171,316 | 10/1979 | Pedersen | 252/437 X |
| 4,178,298 | 12/1979 | Stefani et al. | 252/437 X |
| 4,181,628 | 1/1980 | Stefani et al. | 252/437 X |
| 4,209,423 | 6/1980 | Hutchings et al. | 252/437 X |
| 4,222,945 | 9/1980 | Higgins et al. | 252/437 X |
| 4,288,372 | 9/1981 | Hutchings et al. | 549/259 |
| 4,317,778 | 3/1982 | Blum et al. | 252/437 X |
| 4,328,120 | 5/1982 | Udovich | 252/435 |
| 4,328,126 | 5/1982 | Udovich et al. | 252/435 |
| 4,337,174 | 6/1982 | Nount et al. | 252/435 X |
| 4,361,501 | 11/1982 | Blum et al. | 252/437 X |

*Primary Examiner*—William G. Wright
*Attorney, Agent, or Firm*—David P. Yusko; John E. Miller, Jr.; Larry W. Evans

[57] ABSTRACT

A process is provided for activating fluidizable catalysts containing the mixed oxides of vanadium and phosphorus useful for the production of maleic anhydride from 4-carbon atom hydrocarbons and oxygen by subjecting the catalyst to fluidization conditions and contacting the fluidized catalyst with oxygen at a temperature at least 20° C. greater than the temperature required to produce about 85 percent conversion of hydrocarbon. A process is also provided for adding make-up fluid bed catalyst to an equilibrated catalyst by introducing a calcined and unequilibrated make-up catalyst into the fluid bed vessel containing equilibrated catalyst, subjecting the mixture to fluidization conditions and contacting the fluidized catalyst mixture with oxygen at a temperature at least 20° C. greater than the temperature required to produce about 85 percent conversion of the hydrocarbon. The catalysts so activated and a process for producing maleic anhydride from 4-carbon atom hydrocarbons is also provided.

10 Claims, No Drawings

METHOD FOR ADDING MAKE-UP FLUID BED OXIDATION CATALYSTS FOR FLUID BED OXIDATION CATALYSTS CONTAINING THE MIXED OXIDES OF VANADIUM AND PHOSPHORUS

BACKGROUND OF THE INVENTION

The present invention relates to the activation of fluid bed oxidation catalysts. More particularly the present invention relates to the activation of fluid bed oxidation catalysts useful in the preparation of maleic anhydride from 4-carbon atom hydrocarbons, including n-butane.

Oxidation catalysts containing the mixed oxides of vanadium and phosphorus have been utilized to produce maleic anhydride from 4-carbon atom hydrocarbons, such as n-butane. Methods have been investigated for activating, or increasing the catalytic activity of these catalysts. It is taught in the literature to "condition" vanadium phosphate-containing maleic anhydride catalysts under the flow of a low level of hydrocarbon in air, such as 0.2 volume percent to 2 volume percent hydrocarbon in air at temperatures of 300° C. to 600° C., as in U.S. Pat. No. 4,171,316.

U.S. Pat. No. 3,985,775 discloses the preparation of vanadium phosphorus mixed oxide catalysts prepared by a method requiring heating the catalyst precursor at about 350° C. to 410° C. to drive off at least a portion of hydration, and then at a higher temperature. This method is taught as suitable for use in fixed bed operation.

Attempting to "condition" a fluid bed catalyst with low levels of hydrocarbon in air under normal operating conditions has been found to have little beneficial effect.

Activation procedures for fixed bed catalysts are not readily applicable for use with fluid bed catalysts. In fixed bed operation, a characteristic exotherm or hot spot is generated in the catalyst bed within the reactor vessel. A substantial portion of the total reaction takes place at this hot spot. The location of the hot spot is dependent upon the location of the oxygen and feed stock inlets, the dimensions of the vessel, and operating conditions such as flow rates, temperature and pressure. Fixed bed activation procedures generally may concentrate in the hot spot of the catalyst bed, having little effect on the remainder of the catalyst in the reactor.

In fluid bed operation, such a hot spot is not generated. Catalyst particles are not localized, but move throughout the reactor vessel, and substantially the entire portion of the catalyst within the reactor vessel contacts the feed to contribute to the reaction.

SUMMARY OF THE INVENTION

It is therefore an object of the present invention to achieve activation of substantially the entire portion of fluid bed maleic anhydride catalysts containing the mixed oxides of vanadium and phosphorus within the reactor vessel.

It is a further object of the present invention to activate make-up fluid bed catalyst which has been added to a reactor vessel in the presence of previously equilibrated catalyst.

We have found that fluid bed maleic anhydride catalysts containing the mixed oxides of vanadium and phosphorus can be activated by a method which permits the activation of substantially the entire portion of the catalyst within the reactor vessel by subjecting a fluidizable catalyst to fluidization conditions, and thereafter contacting the fluidized catalyst with oxygen or an oxygen containing gas at a temperature at least 20° C. greater than the temperature required to produce about 85 percent conversion of the hydrocarbon feed stock. In a preferred mode, the fluidized catalyst is contacted with oxygen or an oxygen containing gas and hydrocarbon at a temperature above the normal operating temperature for equilibrated catalysts of the same composition, at which temperature the hydrocarbon is converted substantially to carbon monoxide or carbon dioxide. By "equilibrated catalyst" is meant catalyst which has exhibited stable activity over time for the reaction of 4-carbon atom hydrocarbons to maleic anhydride.

It is necessary in the commercial operation of fluid bed reaction systems, to add additional fresh catalyst (i.e., make-up catalyst) to the reactor vessel from time to time in order to replace catalyst particles which are gradually lost from the fluid bed reactor vessel due either to attrition of the catalyst particles or to inefficiency of reactor cyclones at the top of the fluid bed reactor which return the fluidized catalyst to the reactor vessel. Fresh vanadium and phosphorus mixed oxide containing catalysts do not, however, operate with the same activity as equilibrated catalysts. Fresh catalyst is generally less selective than equilibrated catalyst, and less active. Without activation, the makeup catalyst-equilibrated catalyst mix may never attain the activity of the original equilibrated catalyst.

A method is required to activate the make-up catalyst in order to permit smooth and efficient operation of the reactor system. It is also required that the method used for activating the make-up catalyst not harm the equilibrated catalyst which is present in the reactor vessel.

We have found that the above method permits the activation of make-up catalyst in the presence of equilibrated catalyst without detrimental effect to the equilibrated catalyst. In fact, the subject method may be used to reactivate catalyst which although formerly equilibrated has lost activity due to extended operation or other factors.

In general, the process of the present invention includes activating substantially the entire portion of a catalyst containing the mixed oxides of vanadium and phosphorus useful for the production of maleic anhydride from 4-carbon atom hydrocarbons and oxygen within a fluid bed vessel, comprising charging a fluidizable catalyst to the fluid bed vessel;
subjecting the fluidizable catalyst to fluidization conditions to obtain a fluidized catalyst;
contacting the fluidized catalyst with oxygen or an oxygen containing gas at a temperature at least 20° C. greater than the temperature required to produce about 85 percent conversion of hydrocarbon.

In a preferred mode, the process includes contacting the fluidized catalyst with oxygen or an oxygen containing gas and the hydrocarbon at an activating temperature above the operating temperature for the equilibrated catalyst at which activating temperature the hydrocarbon is converted predominantly to carbon monoxide and carbon dioxide.

In another embodiment of the invention is included a process for adding make-up fluid bed catalyst to an equilibrated fluidizable catalyst comprising the mixed oxides of vanadium and phosphorus useful in oxidizing 4-carbon atom hydrocarbons to maleic anhydride, in a fluid bed vessel including;

introducing a calcined and unequilibrated fluidizable catalyst comprising the mixed oxides of vanadium and phosphorus into the fluid bed vessel containing equilibrated fluidizable catalyst, subjecting the fluidizable make-up and equilibrated catalysts to fluidization conditions to obtain a fluidized catalyst mixture;

contacting the fluidized catalyst mixture with oxygen or an oxygen containing gas at a temperature at least 20° C. greater than the temperature required to produce about 85 percent conversion of hydrocarbon.

In a preferred mode, the invention includes contacting the fluidized catalyst mixture with oxygen and the hydrocarbon at an activating temperature above the operating temperature for equilibrated catalyst at which activating temperature the hydrocarbon is converted predominantly to carbon monoxide and carbon dioxide.

The present invention further provides a fluidizable catalyst containing the mixed oxides of vanadium and phosphorus, activated by the above processes.

The present invention further provides a process for producing maleic anhydride in the vapor phase, utilizing the activated catalyst prepared by the above process.

DETAILED DESCRIPTION OF THE INVENTION

Catalysts for the production of maleic anhydride from 4-carbon atom hydrocarbons, such as n-butane, butenes, and butadiene, particularly n-butane, generally contain the mixed oxides of vanadium and phosphorus. The catalysts may additionally contain promoter elements, including but not limited to alkali or alkaline earth metals, titanium, chromium, tungsten, tantalum, manganese, arsenic, antimony, tellurium, bismuth, tin, germanium, zirconium, hafnium, niobium, molybdenum, iron, cobalt, nickel, copper, zinc, cadmium, rare earths, cerium, uranium, thorium and mixtures thereof. The molar ratio of promoter elements to vanadium is generally 0.001:1 to 1:1, preferably about 0.01:1 to 0.5:1. The molar ratio of phosphorus to vanadium is generally about 0.5:1 to about 2:1, preferably about 0.8:1 to about 1.3:1. The valence of the vanadium component of the catalyst is generally reduced from the pentavalent state, the valence of vanadium generally being between about +3.5 to about +4.6 and preferably being about +4. The maleic anhydride catalyst may additionally contain diluent or supports, such as titania, alumina, alumina-silica, zirconia, boron phosphate, silica, silicon carbide, and the like, and may be impregnated or coated upon such supports.

The catalyst may be prepared by reacting catalyst component containing compounds in the presence or absence of a corrosive reducing agent in a liquid, including but not limited to water, alcohols, aldehydes, glycols, ketones, halogenated olefins, and the like. Suitable corrosive reducing agents to provide vanadium in the proper valence state include but are not limited to HCl, HBr, and oxalic acid. Suitable liquid media capable of reducing vanadium to its proper valence state include but are not limited to isopropanol, isobutanol, crotyl alcohol, allyl alcohol, isopentanol, acetaldehyde, propionaldehyde, butyraldehyde, ethylene glycol, methyl ethyl ketone, perchloropropene, hexachlorobutadiene and the like, and their use is preferred. Additional organic solvents such as benzene, acetic anhydride or dimethyl phthalate can be used in conjunction with the above reducing agents or media.

Suitable vanadium compounds for use in preparing the maleic anhydride catalysts include vanadium pentoxide or vanadium salts, such as ammonium metavanadate and vanadium oxytrihalides. Suitable phosphorus containing compounds include phosphoric acid, including metaphosphoric acid, orthophosphoric acid, triphosphoric acid and pyrophosphoric acid, and phosphorus pentoxide, phosphorus oxiodide, phosphorus oxychloride, phosphorus pentachloride, and the like. Suitable promoter element containing compounds include promoter metal oxides, hydroxides, nitrates, halides, or salts of organic acids such as acetates, formates, butyrates, benzylates, and the like.

The catalyst components are mixed in the liquid medium, before or after the vanadium component is reduced to its proper valence state. The catalyst pecursor formed is recovered and dried. The catalyst is formed into fluid bed form by crushing and screening the catalyst particles to a proper size, such as in the range of about 20 to about 300 microns, by the oil drop method wherein an aqueous solution or slurry of the catalyst is dropped into a heated oil bath to form solid particles, or by spray drying to form the desired particles. The catalyst may be calcined after forming into the fluidizable particles, dependent upon the method of preparation chosen. A method of preparing fluidizable catalysts useful for the production of maleic anhydride from 4-carbon atom hydrocarbons such as n-butane is disclosed in U.S. Pat. No. 4,317,778, assigned to our common assignee, incorporated herein by reference. The specific method of preparing the catalysts to be activated is not, however, critical to the process of the present invention.

Hydrocarbons reacted to form maleic anhydride include n-butane, n-butenes, 1,3 butadiene, or a mixture thereof. The molecular oxygen used in the reaction is most conveniently added as air, but synthetic streams containing molecular oxygen are also suitable. In addition to the hydrocarbon and molecular oxygen, other gases may be added to the reactant feed, such as steam or nitrogen. Preferably, oxygen/hydrocarbon ratios in the reactor feed are about 4 to about 20 moles of oxygen per mole of hydrocarbon.

The reaction temperature may vary widely and is dependent upon the particular hydrocarbon and catalysts employed. Generally, temperatures of about 325° C. to about 450° C. are preferred. The reaction may be conducted at atmospheric, superatmospheric or subatmospheric pressure, although operation at superatmospheric pressure is preferred.

Catalyst Activation

In the process of the present invention, fluidizable catalysts containing the mixed oxides of vanadium and phosphorus are activated such that substantially the entire portion of the catalyst within a fluid bed vessel is subjected to the activating feed and is thus activated. The fluidizable catalyst is charged to a fluid bed vessel, preferably the fluid bed reactor vessel in which the catalyst may be activated in situ. The fluidizable catalyst is then subjected to fluidization conditions in order to fluidize the catalyst. Fluidization conditions can be determined readily by those of skill in the art, and includes the introduction of a gas stream into the catalyst containing fluid bed vessel sufficient to "raise" the catalyst bed and contact substantially all catalyst particles with the feed. The fluidized catalyst is then contacted with oxygen at a temperature at least 20° C. greater than the temperature required to produce about a 85 percent conversion of the hydrocarbon feed stock to be utilized to produce maleic anhydride or other desired products.

Oxygen may be added as air or synthetic streams containing molecular oxygen may be utilized. Inert gases may be added to the activating feed, including but not limited to nitrogen, argon, carbon dioxide, steam, and the like.

The activating feed can include low levels of the hydrocarbon being utilized as a reactant to produce maleic anhydride, such as n-butane, n-butenes and butadiene, in a ratio of up to about 0.1 to about 5, preferably about 0.5 to about 3.5 mole percent hydrocarbon. Should the mixed vanadium phosphorus oxide catalyst be used to catalyze other reactions such as the oxydehydrogenation of ethane to ethylene, the ethane and oxygen feed could be used in the process of the present invention, at elevated temperatures as set forth herein in order to provide the activating feed.

Other hydrocarbons could be added to the feed stock during the activation process, in order to combust with the oxygen in order to provide the required heat to bring the fluid bed vessel to temperature. Such other hydrocarbons may have up to ten carbon atoms and may include methane, ethane, propane, isobutane, isobutylene, pentane, hexane, benzene, and the like. Additionally, hydrogen may be utilized. Up to 5 mole percent hydrogen or hydrocarbon may be utilized in the activating feed.

The fluidizable catalysts of the present invention may be subjected to the activation process, preferably before substantial use as a catalyst for the production of maleic anhydride, or the activation process can be utilized after the catalyst has been used extensively for the production of maleic anhydride.

When a hydrocarbon is utilized with oxygen in the activating feed, the activation procedure is preferably conducted at a temperature above the operating temperature for equilibrated catalyst, at which activating temperature the hydrocarbon is converted predominately to carbon monoxide and carbon dioxide. In this embodiment, the catalyst is operating in an active mode, converting or over-converting the hydrocarbon feed to carbon oxides.

The process of the present invention is additionally suitable to the activation of make-up catalyst which has been added to equilibrated catalyst in the fluid bed reactor vessel. To avoid the necessity for equilibrating the make-up catalyst before addition, and to avoid the reduction of activity for the fresh/equilibrated catalyst mixture, the activation procedure of the present invention may be used. As used herein, a catalyst is equilibrated when the percent conversion is relatively stable over time in a particular temperature regime. In the absence of the activation process of the present invention, the equilibration time for catalysts containing vanadium and phosphorus mixed oxides is generally extensive. If not "activated", the vanadium phosphorus mixed oxide catalyst may never attain optimum equilibration and activity. If make-up catalyst was added to the equilibrated catalyst without subsequent activation, and the make-up catalyst was not activated initially, the activity of the mixed charge would drop with each introduction of fresh catalyst. The make-up catalyst which is added, however, is preferably calcined.

The activation procedures should generally be carried out at a temperature at least 20° C. greater than the temperature required for an equilibrated catalyst to produce about 85 percent conversion of hydrocarbon to maleic anhydride. The activation temperature may be as high as 120° C. greater than the 85 percent conversion level temperature, and is preferably about 40°–80° C. greater. When hydrocarbon is used with oxygen as the activating feed, the activation is preferably carried out at a temperature, above the operating temperature for equilibrated catalyst, at which activation temperature the hydrocarbon is converted predominately to carbon monoxide or carbon dioxide. For example, for catalysts which generally operate within the range between 385° C.–445° C., activation is generally carried out at temperatures of about 450° C.–525° C. and preferably about 460° C.–480° C.

The time required for activation depends in part upon the degree of activation desired and the temperature which the activation is carried out. In general, higher activation temperatures and longer activation time independently contribute to a more activated form of the catalyst. Activation may take place at subatmospheric, atmospheric or superatmospheric pressures.

SPECIFIC EMBODIMENTS

Example 1

A catalyst containing the mixed oxides of vanadium and phosphorus, having a phosphorus to vanadium ratio of 1.2:1 were prepared as described in U.S. Pat. No. 4,317,778, incorporated by reference above. The fluidizable catalyst was used to produce maleic anhydride from n-butane in a 550 cc fluid bed test reactor consisting of about a 61 cm length of stainless steel tubing having an inner diameter of about 4.1 cm, having a stainless steel sparger at the bottom of the tube to act as a gas (air) distributor with an axial 0.64 cm outer diameter thermowell and a separate hydrocarbon inlet at the bottom of the tube. The reactor was fitted with internal gas redistributing baffles. Gas preheating and reactor temperature control was accomplished by placement of the reactor unit in a thermostatic fluidized sand bath.

Flasks for receiving the product maleic anhydride were air cooled, and effluent gases were routed to a gas chromatograph for analysis. Reaction conditions and results of the tests run are described in the Table below. The throughput of hydrocarbon feed in the production of maleic anhydride, or the working rate imposed upon the catalyst can be described as WWH, or weight of hydrocarbon feed/weight of catalyst/hour.

After calcination, the catalyst was charged to the fluid bed test reactor and the catalyst was subjected to a temperature of 480° C. for about 20 hours. The activating feed was a 60/1 mixture of air/butane at a WWH of 0.01. After activation, the temperature and WWH were varied as set forth in Table I. Results of the tests run are reported in the tables below as follows:

$$\text{Single Pass Yield} = \frac{\text{Moles of Maleic Anhydride Fromed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield}}{\text{Total Conversion}}$$

Comparative Example 2

A catalyst was prepared according to the procedure of Example 1, was charged to the fluid bed test reactor and was subjected to a 60/1 hydrocarbon mixture at a WWH of 0.01 at a temperature of 380° C. for about 20 hours. The temperature and WWH was varied as reported in Table I, and results of the tests run are reported in Table I.

Example 3

Catalysts prepared by the procedure of Example 1 were charged to the fluid bed test reactor, a portion of the calcined catalyst being withheld from the reactor for later addition. After equilibration of the catalyst, the feeds were diverted and the catalyst was cooled under a nitrogen stream. 20 percent of the catalyst in the reactor was removed and replaced with the fresh make-up catalyst. The feeds were returned and the activity of the catalyst tested. The equilibrated/fresh catalyst mix was then subjected to activation at a temperature of about 480° C. for about 17 hours. The catalyst was then tested for the production of maleic anhydride after activation. Test conditions and results of the tests run for the production of maleic anhydride from n-butane are contained in Table II.

As is demonstrated in Table I, the process of the present invention provides for a fast activation of fluid bed catalysts containing the mixed oxides of vanadium and phosphorus, such catalysts being subjected to the activation process achieving stable, high yields of maleic anhydride before the same catalyst composition not so activated. As demonstrated in Table II, a mixture of equilibrated and fresh catalyst can be activated using the process of the present invention without harming the equilibrated catalyst.

It is also within the scope of the present invention that a slip stream be provided from the reactor to permit catalyst to be continuously withdrawn, subjected to the activation procedure in a continuous loop and reintroduced into the main reactor continuously while the reactor continues in operation. Such a procedure would permit the maintenance of a high level of activity in the reactor catalyst bed by continuously introducing activated catalysts to the main catalyst bed.

Thus it should be apparent to those skilled in the art that the subject invention accomplishes the objects set forth above. It is to be understood that the subject invention is not to be limited by the examples set forth herein. These have been provided merely to demonstrate operability, and the selection of methods of preparation of the vanadium and phosphorus mixed oxide containing catalysts, the hydrocarbon feed stocks, the activation feeds, molar ratios, and reaction and activation conditions can be determined from the total specification disclosure provided without departing from the spirit of the invention herein disclosed and described, the scope of the invention including equivalent embodiments, modifications and variations that fall within the scope of the attached claims.

TABLE I

PRODUCTION OF MALEIC ANHYDRIDE FROM N—BUTANE USING ACTIVATED $V_1P_{1.2}O_x$ FLUID BED CATALYSTS*

| EXAMPLE NO. RUN | HOURS ONSTREAM | TEMPERATURE (°C.) | WWH | % CONVERSION | MALEIC ANHYDRIDE % YIELD | % SELECTIVITY |
|---|---|---|---|---|---|---|
| 1 ACTIVATION | — | 480 | .01 | 100 | — | — |
| A | 23 | 386 | .01 | 100 | 49.0 | 49.0 |
| B | 27.5 | 392 | .027 | 99.1 | 55.7 | 56.2 |
| C | 97.7 | 424 | .054 | 86.1 | 57.8 | 67.2 |
| D | 116.8 | 431 | .050 | 90.1 | 56.1 | 62.2 |
| COMP. 2 PRE-RUN | — | 383 | .01 | — | — | — |
| A | 19.7 | 383 | .01 | 99.4 | 45.9 | 46.2 |
| B | 66.0 | 419 | .024 | 72.9 | 45.6 | 62.6 |
| C | 95.2 | 430 | .049 | 55.8 | 35.3 | 63.2 |
| D | 114.9 | 431 | .048 | 66.6 | 42.3 | 63.6 |

*AIR/HYDROCARBON Ratio = 60/1

TABLE II

PRODUCTION OF MALEIC ANHYDRIDE FROM N—BUTANE USING $V_1P_{1.2}O_x$ FLUID BED CATALYSTS WITH ACTIVATION AFTER ADDITION OF MAKEUP CATALYST*

| EXAMPLE NO. RUN 3 | HOURS ONSTREAM | TEMPERATURE (°C.) | AIR/HYDROCARBON RATIO | % CONVERSION | MALEIC ANHYDRIDE % YIELD | % SELECTIVITY | % CONVERSION CO | $CO_2$ |
|---|---|---|---|---|---|---|---|---|
| A | 168 | 429 | 25.7 | 87.9 | 54.9 | 62.5 | 17.1 | 14.8 |
| B | 174 | 428 | 27.8 | 89.4 | 54.9 | 61.4 | 17.9 | 15.5 |
| | 175 COOLED REACTOR, REMOVED 20% CATALYST AND REPLACED WITH FRESH CALCINED CATALYST. | | | | | | | |
| C | 178.8 | 422 | 27.8 | 76.5 | 52.8 | 69.0 | 12.2 | 11.6 |
| | 205.7 ACTIVATED AT 480 FOR 17 HOURS. | | | | | | | |
| D | 222.4 | 483 | 29.0 | 100 | 24.4 | 24.4 | 37.9 | 37.6 |
| E | 227.3 | 427 | 29.7 | 90.9 | 54.7 | 60.2 | 18.5 | 16.9 |
| F | 246.6 | 426 | 29.3 | 89.3 | 55.8 | 62.5 | 17.3 | 15.3 |

*WWH EQUALED ABOUT 0.05

We claim:

1. A process adding make-up fluid bed catalyst to an equilibrated fluidizable catalyst containing the mixed oxides of vanadium and phosphorus useful in oxidizing a 4-carbon atom hydrocarbon to maleic anhydride, in a fluid bed vessel including;
   (a) introducing a calcined and unequilibrated fluidizable make-up catalyst comprising the mixed oxides of vanadium and phosphorus into the fluid bed vessel containing the equilibrated fluidizable catalyst;
   (b) subjecting the fluidizable make-up and equilibrated catalysts to fluidization conditions to obtain a fluidized catalyst mixture;

(c) contacting the fluidized catalyst mixture with oxygen at a temperature at least 20° C. greater than the temperature required to produce about 85 percent conversion of the 4-carbon atom hydrocarbon.

2. A process as in claim 1 wherein the activating temperature is between about 20° C. to about 120° C. greater than the temperature required to produce about 85 percent conversion of said 4-carbon atom hydrocarbon.

3. A process as in claim 1 including contacting the fluidized catalyst with said activating feed containing additionally a hydrocarbon, at an activating temperature at which the hydrocarbon is converted predominantly to water, carbon monoxide and carbon dioxide.

4. A process as in claim 3 wherein said activating temperature is between about 450° C. to about 525° C.

5. A process as in claim 3 wherein the activating feed contains between about 0.1 molar percent to about 5 molar percent hydrocarbon.

6. A process as in claim 5 wherein said hydrocarbon is n-butane.

7. A process as in claim 1 wherein the activating feed contains additionally up to 5 molar percent hydrogen.

8. A process as in claim 1 wherein said catalyst contains at least one promoter element selected from alkali metals, alkaline earth metals, titanium, chromium, tungsten, tantalum, manganese, arsenic, antimony, tellurium, bismuth, tin, germanium, zirconium, hafnium, niobium, molybdenum, iron, cobalt, nickel, copper, zinc, cadmium, rare earths, cerium, uranium, thorium and mixtures thereof.

9. A process as in claim 8 wherein the molar ratio of said promoter element to vanadium is between about 0.001:1 to 1:1.

10. A process as in claim 1 wherein the molar ratio of phosphorus to vanadium is about 0.8:1 to about 1.3:1.

* * * * *